United States Patent
Takeda et al.

(10) Patent No.: US 6,229,049 B1
(45) Date of Patent: May 8, 2001

(54) PREPARATION PROCESS OF DIFLUOROACETOPHENONE DERIVATIVE

(75) Inventors: Sunao Takeda; Yasushi Kaneko; Hiromichi Eto; Susumu Sato, all of Narita (JP)

(73) Assignee: SSP Co., Ltd., Tokyo (JP)

( * ) Notice: Subject to any disclaimer, the term of this patent is extended or adjusted under 35 U.S.C. 154(b) by 0 days.

(21) Appl. No.: 09/488,746

(22) Filed: Jan. 21, 2000

(30) Foreign Application Priority Data

Feb. 4, 1999 (JP) .................................................. 11-027147

(51) Int. Cl.⁷ .................................................. C07C 319/14

(52) U.S. Cl. .................................................. 568/43; 568/42

(58) Field of Search ........................................ 568/42, 43

(56) References Cited

U.S. PATENT DOCUMENTS

| | | |
|---|---|---|
| 5,939,448 | 8/1999 | Tokizawa et al. . |
| 5,945,438 | 8/1999 | Tokizawa et al. . |
| 5,986,144 | 11/1999 | Tokizawa et al. . |
| 6,002,028 | 12/1999 | Tokizawa et al. . |
| 6,008,239 | 12/1999 | Kaneko et al. . |
| 6,040,325 * | 3/2000 | Takeda et al. ........................ 514/383 |

OTHER PUBLICATIONS

CA:123:338656 abs of Tetrahedron Lett by Kuroboshi et al 36(34) pp 6121–2, 1995.*

CA:129:244680 abs of Bull Chem Soc Jpn by Furuta et al 71(8) pp 1939–1951, 1998.*

* cited by examiner

*Primary Examiner*—Jean F Vollano
(74) *Attorney, Agent, or Firm*—Oblon, Spivak, McClelland, Maier & Neustadt, P.C.

(57) ABSTRACT

The invention relates to a process for preparing a difluoroacetophenone derivative (4) by alkylthionating a compound (1) into a compound (2) and reacting this compound with a compound (3).

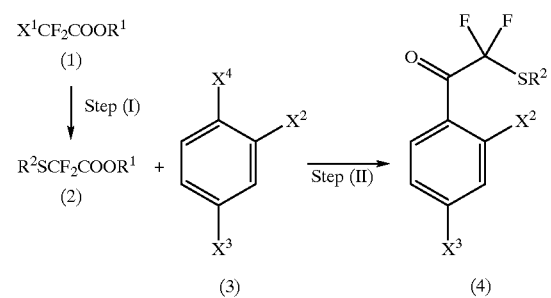

wherein $X^1$ is Cl, Br or I, $X^2$ and $X^3$ are independently a halogen atom, H or perfluoroalkyl group, $X^4$ is a halogen atom, $R^1$ is an alkyl, aryl or aralkyl group, and $R^2$ is methyl, ethyl or cyclopropyl group.

2 Claims, No Drawings

PREPARATION PROCESS OF DIFLUOROACETOPHENONE DERIVATIVE

BACKGROUND OF THE INVENTION

1. Field of the Invention

The present invention relates to a difluoroacetophenone derivative useful as an intermediate for preparation of a triazole derivative having excellent antifungal action and high safety.

2. Description of the Background Art

Triazole derivatives (9a) to (9c) have excellent antifungal action and high safety, are useful as agents for treating mycotic infectious diseases and can be prepared in accordance with the following reaction scheme (see Japanese Patent Application Laid-Open No. 227531/1997, and the like):

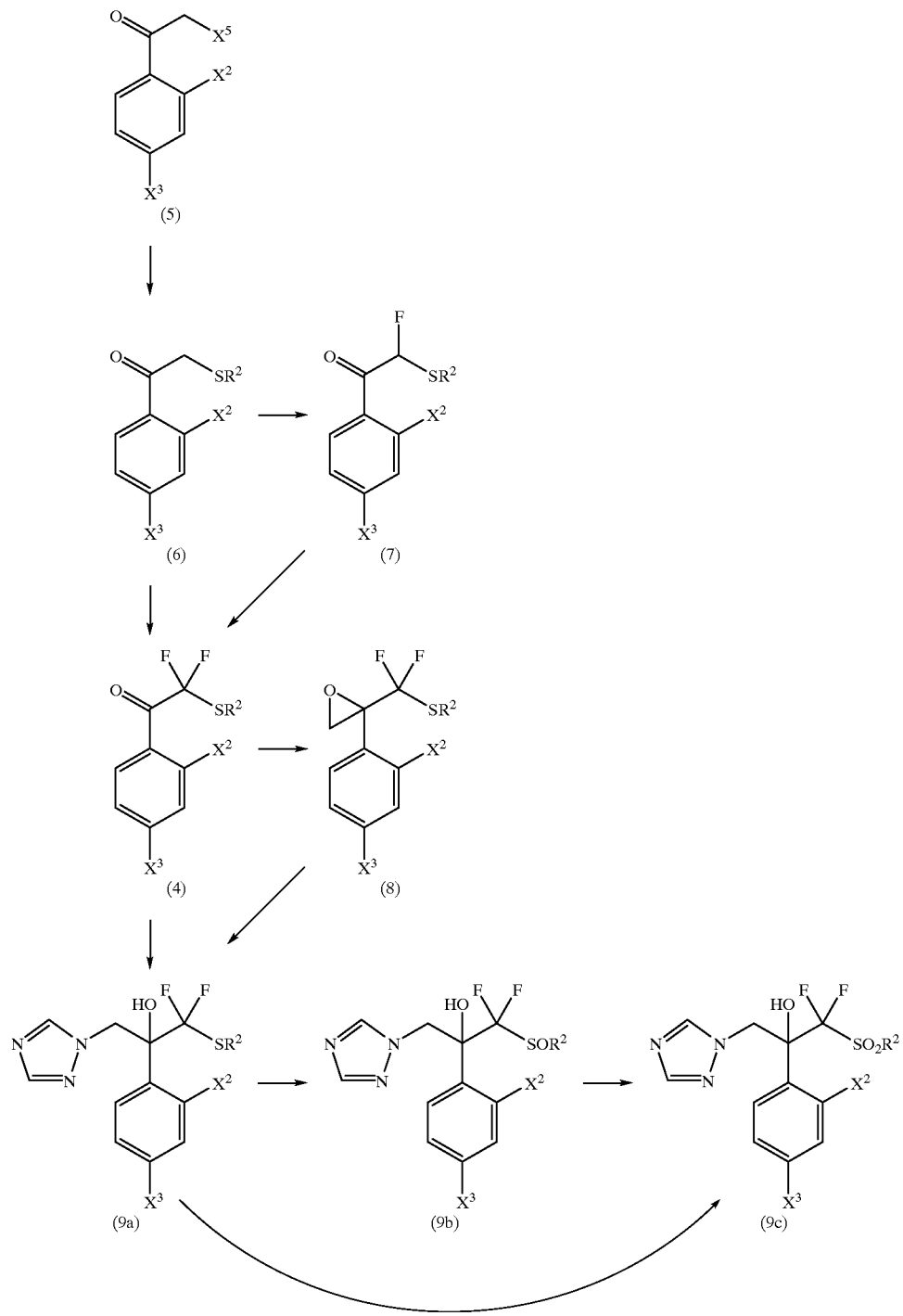

wherein $X^2$ and $X^3$ are the same or different from each other and are independently a halogen or hydrogen atom, or a perfluoroalkyl group, $X^5$ is a halogen atom, and $R^2$ is a methyl, ethyl or cyclopropyl group.

According to this process, a compound (6) or (7) must be fluorinated to give a difluoroacetophenone derivative (4) which is an intermediate for the synthesis.

However, the process of this fluorination has been able to be carried out only in limited facilities for fluorination under severe fluorination conditions using expensive fluorinating reagents.

SUMMARY OF THE INVENTION

It is accordingly an object of the present invention to provide an industrially useful process for preparing the difluoroacetophenone derivative (4).

In view of the foregoing circumstances, the present inventors have carried out an extensive investigation. As a result, it has been found that when a halo-difluoroacetic acid ester, which is easily available, is used as a starting material, this compound is alkylthionated, and the resultant product is coupled to a halobenzene derivative, the difluoroacetophenone derivative (4) can be prepared with industrial advantages, thus leading to completion of the present invention.

The present invention is represented by the following reaction scheme:

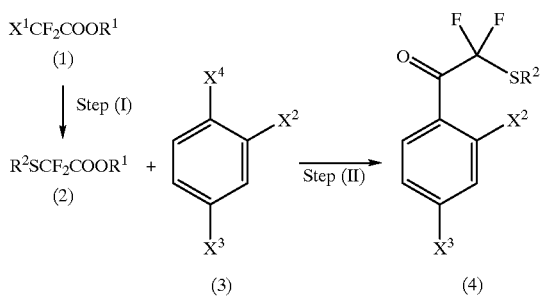

wherein $X^1$ is a chlorine, bromine or iodine atom, $X^4$ is a halogen atom, $R^1$ is an alkyl, aryl or aralkyl group, and $X^2$, $X^3$ and $R^2$ have the same meanings as defined above.

According to the present invention, there is thus provided a process for preparing a difluoroacetophenone derivative represented by the following general formula (4):

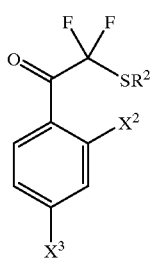

(4)

wherein $R^2$ is a methyl, ethyl or cyclopropyl group, $X^2$ and $X^3$ are the same or different from each other and are independently a halogen or hydrogen atom, or a perfluoroalkyl group, the process comprising coupling an alkylthiodifluoroacetic acid ester derivative represented by the following general formula (2):

$R^2SCF_2COOR^1$ (2)

wherein $R^1$ is an alkyl, aryl or aralkyl group, and $R^2$ has the same meaning as defined above, to a halobenzene derivative represented by the following general formula (3):

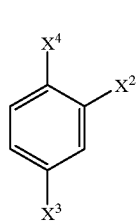

(3)

wherein $X^4$ is a halogen atom, and $X^2$ and $X^3$ have the same meanings as defined above.

According to the present invention, difluoroacetophenone derivatives useful as intermediates for preparation of triazole derivatives (9a) to (9c) having excellent antifungal action can be prepared with industrial advantages.

The above and other objects, features and advantages of the present invention will be readily appreciated as the same becomes better understood from the preferred embodiments of the present invention, which will be described subsequently in detail, and from the appended claims.

DETAILED DESCRIPTION OF THE PREFERRED EMBODIMENTS

The process according to the present invention comprises Step (I) and Step (II) as shown in the above reaction scheme.

Step (I):

The alkylthiodifluoroacetic acid ester derivative of the compound (2) can be prepared by alkylthionating the halodifluoroacetic acid ester derivative represented by the above general formula (1). In the compound (1) which is a starting material, examples of $X^1$ in the general formula (1) include chlorine, bromine and iodine atoms. Of these, a chlorine or bromine atoms is preferred. Examples of $R^1$ include alkyl, aryl and aralkyl groups. Alkyl groups having 1 to 10 carbon atoms are preferred, with lower alkyl groups being particularly preferred. The lower alkyl groups include methyl, ethyl, n-propyl, isopropyl, n-butyl, isobutyl, tert-butyl, n-pentyl and n-hexyl groups, etc. An ethyl group is particularly preferred. The aryl groups include aryl groups having 6 to 14 carbon atoms, for example, phenyl and naphthyl groups. The aralkyl groups include phenyl-$C_{1-6}$-alkyl groups, for example, benzyl and phenylethyl groups, etc.

The process of the alkylthionation can be performed by reacting the compound (1) with methyl mercaptan, ethyl mercaptan or cyclopropyl mercaptan (J. Am. Chem. Soc., 114, 3492 (1992)) in the presence of a base or directly with an alkali metal salt of methyl mercaptan, ethyl mercaptan or cyclopropyl mercaptan. As a reaction solvent, there may be used an alcoholic solvent such as methanol or ethanol; an ethereal solvent such as diethyl ether, 1,4-dioxane or tetrahydrofuran; a non-aqueous polar solvent such as N,N-dimethylformamide or dimethyl sulfoxide; a basic solvent such as pyridine or triethylamine; or a mixed solvent thereof. Dimethyl sulfoxide and a mixed solvent of dimethyl sulfoxide and diethyl ether are particularly preferred. As the base, there may be used an inorganic base such as sodium carbonate, potassium carbonate, sodium hydroxide, potassium hydroxide, barium hydroxide, sodium hydride, sodium methoxide or sodium ethoxide; or an organic base such as pyridine or triethylamine. Sodium hydride is particularly preferred. As the alkali metal salt of the alkyl mercaptan, there may be used the lithium, sodium or potassium salt, with the sodium salt being particularly preferred. The reaction can be carried out at a temperature within a range of from −40° C. to 100° C. The reaction temperature within a range of from −10° C. to 80° C. is particularly preferred.

Step (II):

The compound (4) can be prepared by causing an organometallic reagent to act on the halobenzene derivative (3) to form a metallic compound of the compound (3) and then coupling the metallic compound to the compound (2).

$X^2$ and $X^3$ in the general formula of the halobenzene derivative (3) used herein are independently a halogen atom such as a fluorine, chlorine, bromine or iodine atom, a hydrogen atom, or a perfluoroalkyl group. As the halogen atom, is preferred a fluorine or chlorine atom. Examples of the perfluoroalkyl group include perfluoroalkyl groups having 1 to 6 carbon atoms, with a trifluoromethyl or pentafluoroethyl group being preferred. $X^4$ is a halogen atom such as a fluorine, chlorine, bromine or iodine atom, with a bromine, chlorine or iodine atom being preferred. Incidentally, it is preferred from the viewpoint of yield that $X^4$ be a halogen atom having higher reactivity than $X^2$ and $X^3$. For example, the halogen atom of $X^4$ preferably has a higher atomic weight than the halogen atoms of $X^2$ and $X^3$.

As a solvent used in Step (II), is prefered an ether such as ethyl ether, isopropyl ether, tert-butyl methyl ether or tetrahydrofuran, a hydrocarbon such as pentane or n-hexane, or a mixed solvent thereof. An ethereal solvent, particularly ethyl ether, isopropyl ether or tert-butyl methyl ether is particularly preferred. As the organometallic compound, is preferred n-butyllithium, sec-butyllithium, tert-butyllithium, methyllithium, ethyllithium, phenyllithium, lithiumdiisopropylamide, potassium hexamethyldisilazane or sodium amide, with n-butyllithium being particularly preferred. As a stabilizer for the metallic compound of the compound (3), may be added hexamethylphospholic triamide, tetramethylethylenediamine or the like. The reaction temperature is preferably −100 °C. to 20° C., particularly preferably −78° C. to −20° C.

No particular limitation is imposed on the means isolating the intended product from the reaction mixture in the above reaction, and the isolation can be conducted by, for example, distillation, various kinds of chromatography, and/or the like.

The thus-obtained difluoroacetophenone derivative (4) can be converted into a triazole derivative (9a) by directly triazolylmethylating the compound (4) or once converting it into an epoxy compound (8) and then triazolating this compound in accordance with the above-described reaction scheme. This triazole derivative (9a) can be oxidized into a derivative (9b) and further into a derivative (9c) (see Japanese Patent Application Laid-Open No. 227531/1997 and the like).

The present invention will hereinafter be described in more detail by the following Examples. However, the present invention is not limited to these examples.

EXAMPLE 1

Synthesis of Ethyl 2,2-Difluoro-2-(Methylthio)-Acetate

A solution of ethyl chlorodifluoroacetate (7.9 g, 50.0 mmol) in dimethyl sulfoxide (20 ml) was added dropwise to a solution of sodium methyl mercaptan (4.6 g, 65 mmol) in dimethyl sulfoxide (60 ml) under cooling with ice, and the mixture was stirred at room temperature for 1 hour. After completion of the reaction, the reaction mixture was poured into ice water to conduct extraction with ether. The solvent was distilled out of the resultant extract under reduced pressure. The resultant residue was distilled under reduced pressure to obtain the intended product (3.7 g; yield: 43.2%) as a colorless oil.

Boiling point: 68° C./20 mmHg. $^1$H-NMR (CDCl$_3$): 1.38 (3H,t,J=7.3 Hz), 2.35(3H,s), 4.37(2H,q,J=7.3 Hz).

EXAMPLE 2

Synthesis of Ethyl 2-(Ethylthio)-2,2-Difluoroacetate

Ethyl mercaptan (6.8 g, 109.7 mmol) was added dropwise to a solution of 60% sodium hydride (2.6 g, 65 mmol) in dimethyl sulfoxide (80 ml) under cooling with ice, and the mixture was stirred at room temperature for 10 minutes. A solution of ethyl bromodifluoroacetate (11.2 g, 55.2 mmol) in dimethyl sulfoxide (20 ml) was added dropwise to this solution under cooling with ice, and the resultant mixture was stirred at room temperature for 1 hour. After completion of the reaction, the reaction mixture was poured into ice water to conduct extraction with ether. The solvent was distilled out of the resultant extract under reduced pressure. The resultant residue was distilled under reduced pressure to obtain the intended product (6.8 g; yield: 66.7%) as a colorless oil.

Boiling point: 115–117° C./35 mmHg. $^1$H-NMR (CDCl$_3$): 1.37(6H,t,J=7.0 Hz), 2.91(2H,q,J=7.0 Hz), 4.37(2H,q,J=7.0 Hz).

EXAMPLE 3

Synthesis of Ethyl 2-(Cyclopropylthio)-2,2-Difluoroacetate

An ether solution of cyclopropyl mercaptan synthesized from cyclopropyl bromide (50.0 g, 413 mmol) in accordance with the process described in literature (J. Am. Chem. Soc., 114, 3492 (1992)) was added dropwise to a solution of 60% sodium hydride (5.4 g, 135 mmol) in dimethyl sulfoxide (100 ml) under cooling with ice, and the mixture was stirred at room temperature for 10 minutes. A solution of ethyl bromodifluoroacetate (27.4 g, 135 mmol) in dimethyl sulfoxide (200 ml) was added dropwise to this solution under cooling with ice, and the resultant mixture was stirred at room temperature for 1 hour. After completion of the reaction, the reaction mixture was poured into ice water to conduct extraction with ether. The solvent was distilled out of the resultant extract under reduced pressure. The resultant residue was distilled under reduced pressure to obtain the intended product (12.3 g; yield: 46.0%) as a colorless oil.

Boiling point: 125–130° C./90 mmHg. $^1$H-NMR (CDCl$_3$): 0.7–1.1(4H,m), 1.38(3H,t,J=7.0 Hz), 1.9–2.3(1H, m), 4.37(2H,q,J=7.0 Hz).

EXAMPLE 4

Synthesis of 1-(2,4-Difluorophenyl)-2,2-Difluoro-2-(Methylthio)-1-Ethanone

A hexane solution (13.7 ml, 21.6 mmol) of 1.58 M n-butyllithium was added dropwise to a solution of 1-bromo-2,4-difluorobenzene (4.2 g, 21.8 mmol) in absolute ether (60 ml) at −70° C., and the mixture was stirred for 15 minutes at the same temperature. A solution of ethyl 2,2-difluoro-2-(methylthio)acetate (3.7 g, 21.6 mmol) in absolute ether (20 ml) was added to this solution at −70° C. After the resultant mixture was stirred for 1 hour at the same temperature, the temperature of the reaction mixture was raised to 0° C. for 1 hour. The reaction mixture was poured into diluted hydrochloric acid-containing ice to conduct extraction with ether. After the resultant ether solution was washed with water and dried, the solvent was distilled off. The resultant residue was purified by distillation under reduced pressure to obtain 1-(2,4-difluorophenyl)-2,2-difluoro-2-(methylthio)-1-ethanone (4.1 g, yield: 90.0%) as a colorless oil.

Boiling point: 90° C./2 mmHg. $^1$H-NMR (CDCl$_3$): 1.37 (3H,t,J=7.5 Hz), 2.91(2H,q,J=7.5 Hz), 6.7–7.2(2H,m), 7.8–8.2(1H,m).

EXAMPLE 5

Synthesis of 1-(2,4-Difluorophenyl)-2-(Ethylthio)-2,2-Difluoro-1-Ethanone 1-(2,4-Difluorophenyl)-2-(ethylthio)-2,2-difluoro-1-ethanone was obtained as a colorless oil in the same manner as in Example 4 except that ethyl 2-(ethylthio)-2,2-difluoroacetate was used in place of ethyl 2,2-difluoro-2-(methylthio)acetate. (yield: 78.2%)

Boiling point: 90–95° C./2 mmHg. $^1$H-NMR (CDCl$_3$): 2.35(3H,s), 6.7–7.1(2H,m), 7.8–8.2(1H,m).

EXAMPLE 6

Synthesis of 2-(Cyclopropylthio)-1-(2,4-Difluorophenyl)-2,2-Difluoro-1-Ethanone 2-(Cyclopropylthio)-1-(2,4-difluorophenyl)-2,2-difluoro-1-ethanone was obtained as a colorless oil in the same manner as in Example 4 except that ethyl 2-(cyclopropylthio)-2,2-difluoroacetate was used in place of ethyl 2,2-difluoro-2-(methylthio)acetate. (yield: 57.0%)

Boiling point: 150° C./10 mmHg. $^1$H-NMR (CDCl$_3$): 0.6–1.1(4H,m), 1.9–2.2(1H,m), 6.7–7.1(2H,m), 7.8–8.2(1H, m).

EXAMPLE 7

Synthesis of 2,2-Difluoro-1-(4-Fluorophenyl)-2-(Methylthio)-1-Ethanone 2,2-Difluoro-1-(4-fluorophenyl)-2-(methylthio)-1-ethanone was obtained as a colorless oil in the same manner as in Example 4 except that 1-bromo-4-fluorobenzene was used in place of 1-bromo-2,4-difluorobenzene. (yield: 59.8%)

Boiling point: 80–83° C./2 mmHg. $^1$H-NMR (CDCl$_3$): 2.37(3H,s), 7.18(2H,t,J=8.4 Hz), 8.0–8.3(2H,m).

EXAMPLE 8

Synthesis of 2-(Ethylthio)-2,2-Difluoro-1-(4-Fluorophenyl)-1-Ethanone 2-(Ethylthio)-2,2-difluoro-1-(4-fluorophenyl)-1-ethanone was obtained as a colorless oil in the same manner as in Example 4 except that 1-bromo-4-fluorobenzene was used in place of 1-bromo-2,4-difluorobenzene, and ethyl 2-(ethylthio)-2,2-difluoroacetate was used in place of ethyl 2,2-difluoro-2-(methylthio)-acetate. (yield: 63.9%)

Boiling point: 83–85° C./2 mmHg. $^1$H-NMR (CDCl$_3$): 1.38(3H,t,J=7.3 Hz), 2.93(2H,q,J=7.3 Hz), 7.17(2H,t,J=8.6 Hz), 8.0–8.3(2H,m).

EXAMPLE 9

Synthesis of 2-(Cyclopropylthio)-2,2-Difluoro-1-(4-Fluorophenyl)-1-Ethanone 2-(Cyclopropylthio)-2,2-difluoro-1-(4-fluorophenyl)-1-ethanone was obtained as a colorless oil in the same manner as in Example 4 except that 1-bromo-4-fluorobenzene was used in place of 1-bromo-2,4-difluorobenzene, and ethyl 2-(cyclopropylthio)-2,2-difluoroacetate was used in place of ethyl 2,2-difluoro-2-(methylthio)acetate. (yield: 24.0%)

Boiling point: 90–93° C./5 mmHg. $^1$H-NMR (CDCl$_3$): 0.6–1.1(4H,m), 1.9–2.2(1H,m), 7.18(2H,t,J=8.1 Hz), 8.1–8.3(2H,m).

EXAMPLE 10

Synthesis of 2,2-Difluoro-2-(Methylthio)-1-[4-(Trifluoromethyl)Phenyl]-1-Ethanone 2,2-Difluoro-2-(methylthio)-1-[4-(trifluoromethyl) phenyl]-1-ethanone was obtained as a colorless oil in the same manner as in Example 4 except that 1-bromo-4-(trifluoromethyl)benzene was used in place of 1-bromo-2,4-difluorobenzene. (yield: 78.3%)

Boiling point: 92–95° C./8 mmHg. $^1$H-NMR (CDCl$_3$): 2.39(3H,s), 7.77(2H,d,J=8.4 Hz), 8.25(2H,d,J=8.4 Hz).

What is claimed is:

1. A process for preparing a difluoroacetophenone derivative represented by the following general formula (4):

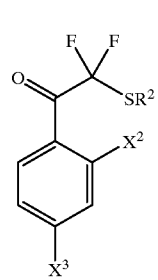

(4)

wherein R$^2$ is a methyl, ethyl or cyclopropyl group, X$^2$ and X$^3$ are the same or different from each other and are independently a halogen or hydrogen atom, or a perfluoroalkyl group, the process comprising coupling an alkylthiodifluoroacetic acid ester derivative represented by the following general formula (2):

R$^2$SCF$_2$COOR$^1$ (2)

wherein R$^1$ is an alkyl, aryl or aralkyl group, and R$^2$ has the same meaning as defined above, to a halobenzene derivative represented by the following general formula (3):

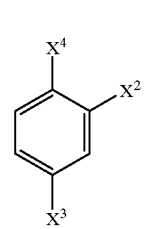

(3)

wherein X$^4$ is a halogen atom, and X$^2$ and X$^3$ have the same meanings as defined above.

2. The process according to claim 1, wherein the alkylthiodifluoroacetic acid ester derivative represented by the general formula (2) is obtained by alkylthionating a halodifluoroacetic acid ester derivative represented by the following general formula (1):

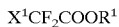

X$^1$CF$_2$COOR$^1$ wherein X$^1$ is a chlorine, bromine or iodine atom, and R$^1$ is an alkyl, aryl or aralkyl group.

* * * * *